United States Patent [19]
Anderson et al.

[11] Patent Number: 5,650,214
[45] Date of Patent: Jul. 22, 1997

[54] WEB MATERIALS EXHIBITING ELASTIC-LIKE BEHAVIOR AND SOFT, CLOTH-LIKE TEXTURE

[75] Inventors: Barry J. Anderson, Loveland; David J. K. Goulait; Sheila S. Rodriguez, both of Cincinnati, all of Ohio

[73] Assignee: The Procter & Gamble Company, Cincinnati, Ohio

[21] Appl. No.: 656,129

[22] Filed: May 31, 1996

[51] Int. Cl.$^6$ .................................................. B32B 3/28
[52] U.S. Cl. .................. 428/152; 428/156; 428/167; 428/212; 428/910; 428/913; 604/358
[58] Field of Search .................. 428/152, 156, 428/167, 212, 910, 913; 604/358

[56] References Cited

U.S. PATENT DOCUMENTS

| | | |
|---|---|---|
| 235,449 | 12/1880 | Newton . |
| 659,266 | 10/1900 | Stewart . |
| 728,828 | 5/1903 | Arkell . |
| 782,977 | 2/1905 | Madden . |
| 1,507,949 | 9/1924 | Angier . |
| 1,582,842 | 4/1926 | Lorenz . |
| 2,007,047 | 7/1935 | Gibbs ............................ 154/33 |
| 2,158,929 | 5/1939 | Dunajeff ........................ 29/180 |
| 2,177,490 | 10/1939 | Kieffer ........................... 154/33 |
| 2,257,428 | 9/1941 | Ruegenberg .................... 154/55 |
| 2,679,887 | 6/1954 | Doyle et al. ................. 154/33.05 |
| 2,896,692 | 7/1959 | Villoresi ..................... 154/33.05 |
| 2,901,951 | 9/1959 | Hochfeld ......................... 93/84 |
| 2,974,716 | 3/1961 | Fourness ....................... 154/31 |
| 3,151,947 | 10/1964 | Hastings ........................ 29/180 |
| 3,236,718 | 2/1966 | Chohn et al. ................. 161/128 |
| 3,313,080 | 4/1967 | Gewiss ......................... 52/618 |
| 3,351,441 | 11/1967 | Gewiss .......................... 29/183 |
| 3,362,118 | 1/1968 | Brunner .......................... 52/284 |
| 3,542,634 | 11/1970 | Such et al. ..................... 161/88 |
| 3,550,423 | 12/1970 | Gewiss .......................... 72/363 |
| 3,726,408 | 4/1973 | Gewiss ......................... 210/493 |
| 3,817,827 | 6/1974 | Benz ............................ 162/113 |
| 3,828,784 | 8/1974 | Zoephel ........................ 128/287 |
| 3,843,761 | 10/1974 | Bierenbaum et al. ............ 264/210 R |
| 3,860,003 | 1/1975 | Buell ........................... 128/287 |
| 3,894,352 | 7/1975 | Hooker .......................... 46/1 L |
| 3,929,135 | 12/1975 | Thompson ...................... 128/287 |
| 3,969,473 | 7/1976 | Meek ........................... 264/90 |
| 3,975,455 | 8/1976 | Falender et al. ................ 260/827 |
| 3,992,162 | 11/1976 | Gewiss ........................ 29/193.5 |
| 4,082,877 | 4/1978 | Shadle .......................... 428/35 |
| 4,101,625 | 7/1978 | Haley .......................... 264/287 |
| 4,104,430 | 8/1978 | Fenton ......................... 428/175 |
| 4,110,391 | 8/1978 | Berzen et al. .................. 264/120 |
| 4,153,664 | 5/1979 | Sabee .......................... 264/289 |
| 4,321,924 | 3/1982 | Ahr ............................ 128/287 |
| 4,324,246 | 4/1982 | Mullane et al. ................ 128/287 |
| 4,342,314 | 8/1982 | Radel et al. ................... 128/287 |
| 4,425,130 | 1/1984 | DesMarais ...................... 604/389 |
| 4,463,045 | 7/1984 | Ahr et al. ..................... 428/131 |
| 4,554,121 | 11/1985 | Kramers ........................ 264/103 |
| 4,589,876 | 5/1986 | Van Tilburg .................... 604/385 |
| 4,609,518 | 9/1986 | Curro et al. ................... 264/504 |
| 4,617,241 | 10/1986 | Mueller ........................ 428/520 |
| 4,640,859 | 2/1987 | Hansen et al. .................. 428/105 |

(List continued on next page.)

FOREIGN PATENT DOCUMENTS

| | | |
|---|---|---|
| 0 307 871 B1 | 12/1992 | European Pat. Off. . |
| WO93/25171 | 12/1991 | WIPO . |

*Primary Examiner*—James J. Bell
*Attorney, Agent, or Firm*—Kevin C. Johnson; Steven W. Miller; Jacobus C. Rasser

[57] ABSTRACT

A soft web material which exhibits an elastic-like behavior along at least one axis when subjected to an applied and subsequently released elongation. The web material includes a strainable network having a plurality of first regions and a plurality of second regions of the same material composition. A portion of the first regions extend in a first direction while the remainder extend in a second direction perpendicular to the first direction to intersect one another. The first regions form a boundary completely surrounding the second regions. The second regions include a plurality of raised rib-like elements.

30 Claims, 7 Drawing Sheets

U.S. PATENT DOCUMENTS

| | | | |
|---|---|---|---|
| 4,719,261 | 1/1988 | Bunnelle et al. | 525/97 |
| 4,780,344 | 10/1988 | Hoberman | 428/12 |
| 4,834,741 | 5/1989 | Sabee | 604/385.2 |
| 4,950,264 | 8/1990 | Osborn | 604/385.1 |
| 4,968,313 | 11/1990 | Sabee | 604/385.2 |
| 5,006,394 | 4/1991 | Baird | 428/138 |
| 5,008,140 | 4/1991 | Schmertz | 428/179 |
| 5,028,474 | 7/1991 | Czaplicki | 428/178 |
| 5,034,078 | 7/1991 | Hodgson, Jr. et al. | 156/85 |
| 5,125,918 | 6/1992 | Seidy | 604/386 |
| 5,143,774 | 9/1992 | Cancio et al. | 428/169 |
| 5,151,092 | 9/1992 | Buell et al. | 604/385.2 |
| 5,196,000 | 3/1993 | Clear et al. | 604/385.2 |
| 5,202,173 | 4/1993 | Wu et al. | 428/131 |
| 5,209,801 | 5/1993 | Smith | 156/161 |
| 5,234,422 | 8/1993 | Sneller et al. | 604/385.2 |
| 5,254,111 | 10/1993 | Cancio et al. | 604/385 |
| 5,268,213 | 12/1993 | Murakami et al. | 428/163 |
| 5,296,184 | 3/1994 | Wu et al. | 264/154 |
| 5,344,691 | 9/1994 | Hanschen et al. | 428/152 |
| 5,422,178 | 6/1995 | Swenson et al. | 428/343 |

WEB MATERIALS EXHIBITING ELASTIC-LIKE BEHAVIOR AND SOFT, CLOTH-LIKE TEXTURE

FIELD OF THE INVENTION

The present invention relates to web materials, and more particularly, to such web materials which exhibit an elastic-like behavior in response to an applied and subsequently released (i.e., cycled) elongation along at least one axis.

The present invention has further relation to web materials which are soft, cloth-like in texture, and quiet.

The present invention has further relation to web materials wherein the inherent properties of a given web material, e.g., the resistive force exerted by the web material to an applied elongation can be modified. Additionally, staged resistive forces, lateral contraction, and/or direction of elastic-like behavior of conventional web materials can also be modified and/or provided as desired in web materials of the present invention.

Web materials of the present invention have a wide range of potential uses in both durable and disposable articles, but are particularly well suited for use in disposable absorbent articles such as sanitary napkins, bandages, pantiliners, disposable diapers, incontinent briefs, and the like.

BACKGROUND OF THE INVENTION

Absorbent articles such as sanitary napkins, pantiliners, disposable diapers, incontinent briefs, and bandages are designed to absorb and retain liquid and other discharges from the human body and to prevent body and clothing soiling. Typically, most disposable absorbent articles are made of materials that will not readily stretch under the forces that the absorbent article is normally subjected to when worn. The inability of the materials comprising the absorbent article to stretch when subjected to normal wearing forces causes the absorbent article to have certain drawbacks. One drawback is the lack of comfort for the wearer. The wearer should ideally be able to notice a difference between an absorbent article that stretches to conform to the wearer's body with the wearer's movements and an absorbent article that fails to stretch. For example, a conventional prior art sanitary napkin does not move with the wearer's undergarments, thereby causing the sanitary napkin to shift which may cause a degree of discomfort for the wearer. Enabling all or a portion of a sanitary napkin to stretch under normal wearing conditions and forces will permit the sanitary napkin to better conform to the wearer's undergarment and stay in place even when the wearer moves.

Several attempts have been made to make one or more components of absorbent articles stretchable in response to relatively low wearing forces. Typical prior art solutions rely on the addition of traditional elastics such as natural or synthetic rubber. For example, traditional elastics have been secured to portions of the topsheet and/or backsheet of absorbent articles, such as the waist portion of a disposable diaper, to provide a better fit and overall comfort for the wearer. However, traditional elastics are costly and require a certain degree of manipulation and handling during assembly. While traditional elastics do provide a degree of stretch for the absorbent article, the materials to which the traditional elastic is secured are typically not normally considered elastic or stretchable. Therefore, the added traditional elastics must be prestretched prior to being secured to the material or the material must be subjected to mechanical processing, e.g., ring rolling, to permanently elongate the material to extend beyond its initial untensioned length and allow the added traditional elastic to be effective. Otherwise, the added traditional elastic is restrained by the material and is rendered inoperable. An example of an absorbent article having a web material which has been subjected to additional processing to allow the web material to more easily extend with the added traditional elastic member is disclosed in U.S. Pat. No. 5,151,092 issued to Buell et al. on Sep. 29, 1992 and hereby incorporated herein by reference. The Buell patent describes an operation which prestrains a backsheet so that the backsheet will, upon mechanical stretching, be permanently elongated and not fully return to its original undistorted configuration. Buell teaches that a traditional elastic member must be added to the prestrained backsheet material for the invention to be operable. Buell also discloses that a prestrained backsheet improves the extension and the heat-shrink contraction of the added traditional elastic member.

Accordingly, it is an object of the present invention to provide web materials, in particular plastic films, which exhibit an "elastic-like" behavior in the direction of applied elongation without the use of added traditional elastic. As used herein, the term "elastic-like" describes the behavior of web materials which when subjected to an applied elongation, the web materials extend in the direction of applied elongation and when the applied elongation is released the web materials return, to a substantial degree, to their untensioned condition. While such web materials exhibiting an elastic-like behavior have a wide range of utility, e.g. durable articles of apparel, disposable articles of apparel, covering materials such as upholstery, wrapping materials for complex shapes and the like, they are particularly well suited for use as a topsheet, a backsheet, and/or an absorbent core in an absorbent article.

It is another object of the present invention to provide plastic films which exhibit a soft, cloth-like texture.

SUMMARY OF THE INVENTION

The present invention pertains, in a preferred embodiment, to a web material, preferably a plastic film, which exhibits an elastic-like behavior in response to an applied and subsequently released elongation without the addition of traditional elastic materials such as natural or synthetic rubber.

In addition, the plastic films of this invention are extremely soft, cloth-like in texture and quiet. The films of this invention provide a barrier against liquid and yet have the appearance and feel of woven or nonwoven fabrics making them especially well suited for use as a backsheet on a disposable absorbent article, such as a disposable diaper or sanitary napkin. Alternatively, the film may be selectively perforated to meet the demands of the breathable films.

Another elastic-like behavior that can be exhibited is an elongation and recovery with a definite and sudden increase in the force resisting elongation where this definite and sudden increase in resistive force restricts further elongation against relatively small elongation forces. The definite and sudden increase in the force resisting elongation is referred to as a "force wall". As used herein, the term "force wall" refers to the behavior of the resistive force of a web material during elongation wherein at some point in the elongation, distinct from the untensioned or starting point, the force resisting the applied elongation suddenly increases. After reaching the force wall, additional elongation of the web material is only accomplished via an increase in the elongation force to overcome the higher resistive force of the web material.

The web material of the present invention includes a strainable network comprising a plurality of first regions and a plurality of second regions being comprised of the same material composition. A portion of the first regions extend in a first direction while the remainder of the first regions extend in a second direction perpendicular to the first direction. The first regions extending in perpendicular directions intersect one another. The first regions form a boundary completely surrounding the second regions. The first regions are oriented relative to an axis of elongation such that they will undergo a substantially molecular-level and geometric deformation in response to an applied axial elongation in a direction substantially parallel to the elongation axis before a substantial portion of the second region undergoes any substantial molecular-level deformation. The second regions initially undergo a substantially geometric deformation in response to an applied elongation.

In a particularly preferred embodiment, the second region is comprised of a plurality of raised rib-like elements. As used herein, the term "rib-like element" refers to an embossment, debossment or combination thereof which has a major axis and a minor axis. The major axes of the rib-like elements are preferably oriented substantially perpendicular to the axis of applied elongation. The major axis and the minor axis of the rib-like elements may each be linear, curvilinear or a combination of linear and curvilinear.

The rib-like elements allow the second region to undergo a substantially "geometric deformation" which results in significantly less resistive forces to an applied elongation than that exhibited by the "molecular-level deformation" and "geometric deformation" of the first region. As used herein, the term "molecular-level deformation" refers to deformation which occurs on a molecular level and is not discernible to the normal naked eye. That is, even though one may be able to discern the effect of molecular-level deformation, e.g., elongation of the web material, one is not able to discern the deformation which allows or causes it to happen. This is in contrast to the term "geometric deformation". As used herein the term "geometric deformation" refers to deformations of the web material which are generally discernible to the normal naked eye when the web material or articles embodying the web material are subjected to an applied elongation. Types of geometric deformation include, but are not limited to bending, unfolding, and rotating.

In another preferred embodiment, the web material of the present invention exhibits at least two significantly different stages of resistive force to an applied elongation along at least one axis when subjected to an applied elongation in a direction substantially parallel to the axis. The web material includes a strainable network having at least two distinct regions. One of the regions is configured such that it will exhibit resistive forces in response to an applied axial elongation in a direction substantially parallel to the axis before a substantial portion of the other region develops any significant resistive force to the applied elongation. At least one of the regions has a surface-pathlength which is greater than that of the other region as measured substantially parallel to the axis while the material is in an untensioned condition. The region exhibiting the longer surface-pathlength includes one or more rib-like elements which extend beyond the plane of the other region. The web material exhibits first resistive forces to the applied elongation until the elongation of the web material is sufficient to cause a substantial portion of the region having the longer surfaces-pathlength to enter the axis of applied elongation, (i.e., become essentially coplanar with the axis of applied elongation), whereupon the web of material exhibits second resistive forces to further elongation. The total resistive force to elongation is higher than the first resistive force to elongation provided by the first region.

Preferably, the first region has a first surface-pathlength, L1, as measured substantially parallel to the axis of elongation while the web material is in an untensioned condition. The second region has a second surface-pathlength, L2, as measured substantially parallel to the axis of elongation while the web is in an untensioned condition. The first surface-pathlength, L1, is less than the second surface-pathlength, L2. The first region preferably has an elastic modulus, E1, and a cross-sectional area, A1. The first region produces by itself a resistive force, P1, due to molecular-level deformation in response to an applied axial elongation, D. The second region preferably has an elastic modulus, E2, and a cross-sectional area, A2. The second region produces a resistive force, P2, due to geometric deformation in response to the applied axial elongation, D. The resistive force, P1, is significantly greater than the resistive force, P2, so long as (L1+D) is less than L2.

Preferably, when (L1+D) is less than L2 the first region provides an initial resistive force, P1, in response to the applied axial elongation, D, substantially satisfying the equation P1=(A1×E1×D)/L1. When (L1+D) is greater than L2 the first and second regions provide a combined total resistive force, PT, to the applied axial elongation, D, satisfying the equation:

$$PT=(A1{\times}E1{\times}D)/L1+(A2{\times}E2{\times}|L1+D-L2|)/L2$$

In another preferred embodiment, the web material exhibits a Poisson lateral contraction effect less than about 0.4 at 20% elongation as measured perpendicular to the axis of elongation. As used herein, the term "Poisson lateral contraction effect" describes the lateral contraction behavior of a material which is being subjected to an applied elongation. Preferably, the web material exhibits a Poisson lateral contraction effect less than about 0.4 at 60% elongation as measured perpendicular to the axis of elongation.

Preferably, the surface-pathlength of the second region is at least about 15% greater than that of the first region as measured parallel to the axis of elongation while the web material is in an untensioned condition. More preferably, the surface-pathlength of the second region is at least about 30% greater than that of the first region as measured parallel to the axis of elongation while the web is in an untensioned condition.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numerals identify like elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinent briefs, bandages, and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). Because of their single use nature, low cost materials and methods of construction are highly desirable in disposable absorbent articles.

Figure 1:
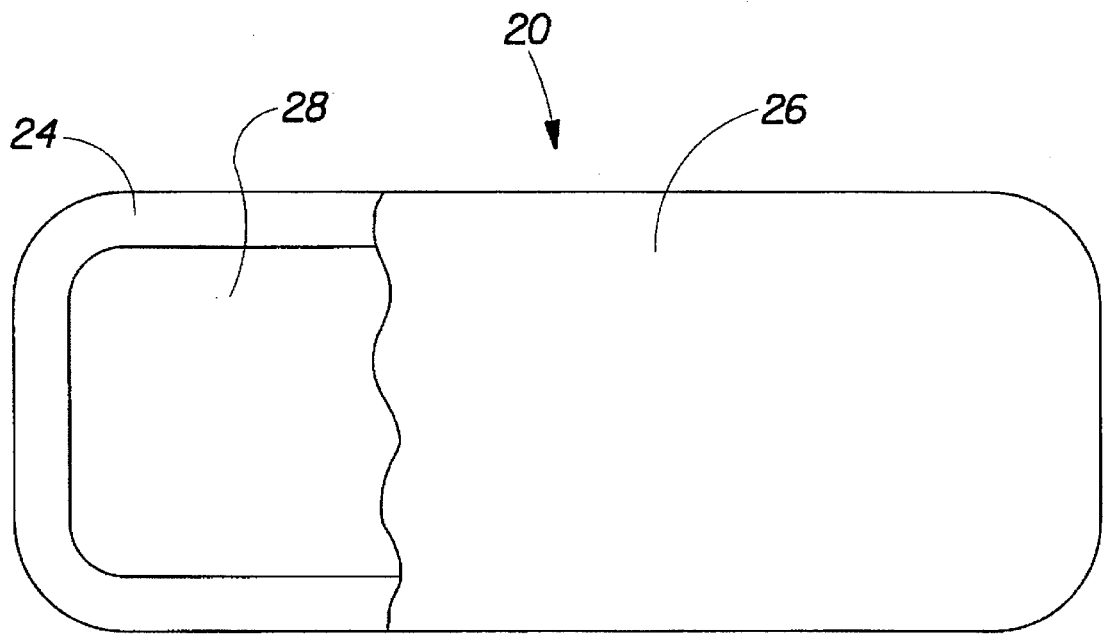
FIG. 1 is a simplified plan view illustration of a prior art sanitary napkin with portions cut-away to more clearly show the construction of the sanitary napkin.

FIG. 1 is a plan view of a prior art sanitary napkin 20 with portions of the structure being cut-away to more clearly show the construction of the sanitary napkin 20 and with the portion of the sanitary napkin 20 which faces away from the wearer, i.e., the outer surface, oriented towards the viewer. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). As shown in FIG. 1, the sanitary napkin 20 comprises a liquid pervious topsheet 24, a liquid impervious backsheet 26 joined with the topsheet 24, and an absorbent core 28 positioned between the topsheet 24 and the backsheet 26.

While the topsheet, backsheet, and absorbent core may be assembled in a variety of well known configurations (including so called "tube" products or side flap products), preferred sanitary napkin configurations are described generally in U.S. Pat. No. 4,950,264, issued to Osborn on Aug. 21, 1990; U.S. Pat. No. 4,425,130, issued to DesMarais on Jan. 10, 1984; U.S. Pat. No. 4,321,924, issued to Ahr on Mar. 30, 1982; and U.S. Pat. No. 4,589,876, issued to Van Tilburg on May 20, 1986. Each of these patents are hereby incorporated herein by reference.

Figure 2:
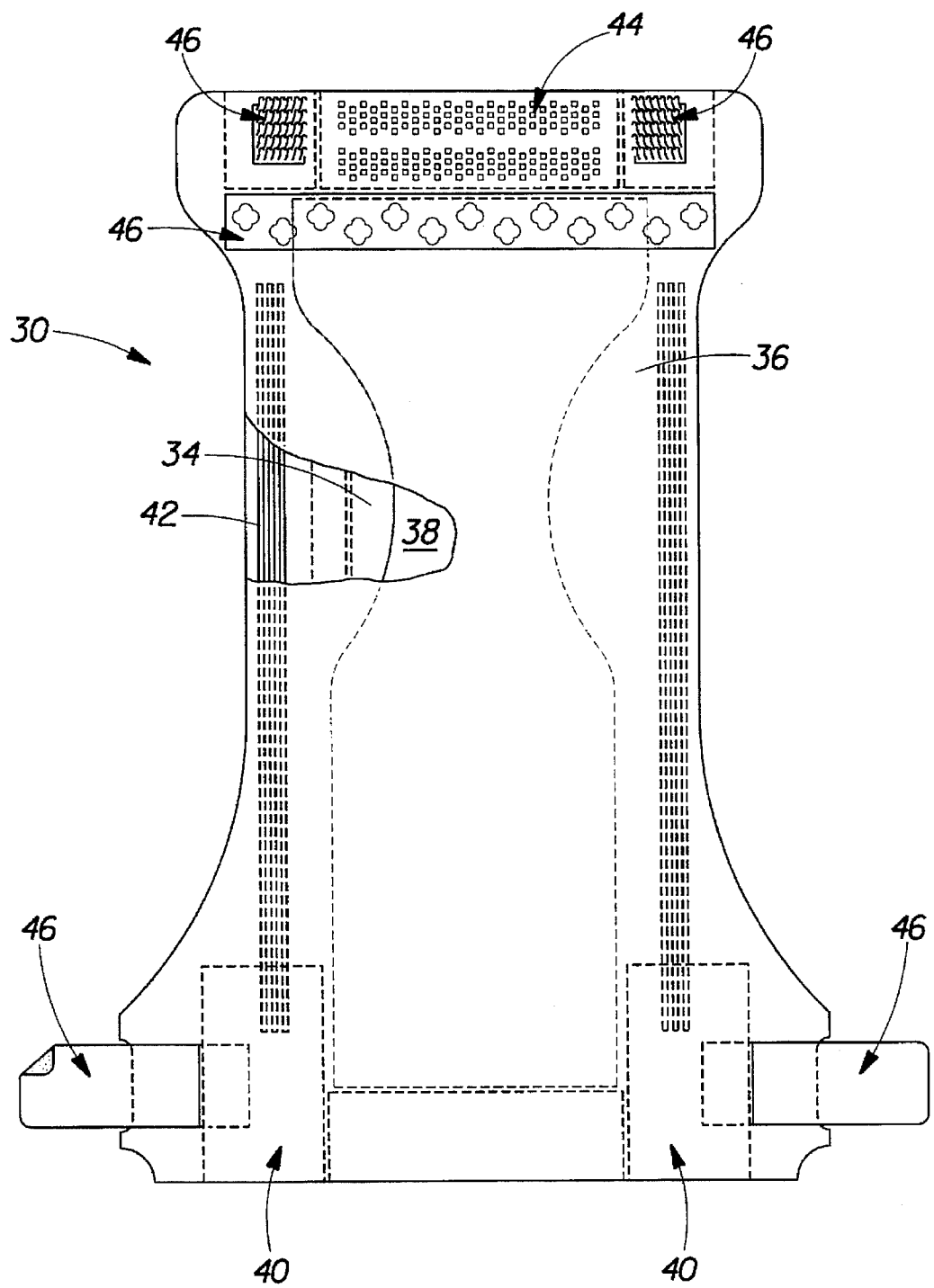
FIG. 2 is a simplified plan view illustration of a prior art disposable diaper with portions cut-away to more deafly show the construction of the disposable diaper.

FIG. 2 is a plan view of a prior art disposable diaper 30 in its uncontracted state (i.e., with elastic induced contraction pulled out except in the side panel wherein the elastic is left in its relaxed condition) with portions of the structure being cut-away to more clearly show the construction of the diaper 30 and with the portion of the diaper 30 which faces away from the wearer, i.e., the outer surface, oriented towards the viewer. As used herein, the term "diaper" refers to an absorbent article generally worn by infants and incontinent persons that is worn about the lower torso of the wearer. As shown in FIG. 2, the diaper 30 comprises a liquid pervious topsheet 34, a liquid impervious backsheet 36 joined with the topsheet 34, an absorbent core 38 positioned between the topsheet 34 and the backsheet 36, elasticized side panels 40, elasticized leg cuffs 42, an elastic waist feature 44, and a fastening system generally multiply designated as 46.

While the diaper 30 may be assembled in a variety of well known configurations, preferred diaper configurations are described generally in U.S. Pat. No. 3,860,003, issued to Kenneth B. Buell on Jan. 14, 1975; and U.S. Pat. No. 5,151,092 issued to Kenneth B. Buell et al. on Sep. 29, 1992. Each of these patents are hereby incorporated herein by reference.

While the present invention will be described in the context of providing a "web material" which exhibits elastic-like behavior to an applied and subsequently released elongation which is particularly well suited for use as a backsheet, a topsheet and/or an absorbent core or a portion thereof on a disposable absorbent article such as a disposable diaper, sanitary napkin, or bandage the present invention is in no way limited to such application. It may be employed in nearly any application where a relatively low cost elastic-like web material is desired, e.g., durable articles of apparel, such as exercise clothing, disposable articles of apparel, elastic bandages, upholstery or wrapping material used to cover complex shaped articles, etc. As used herein the term "web material" refers to a sheet-like material, e.g., a topsheet, backsheet, or absorbent core on a disposable absorbent article, a composite or laminate of two or more sheet-like materials and the like. The present invention may be practiced to great advantage in many situations where it is desirable to produce a web material which exhibits an elastic-like behavior to an applied and subsequently released elongation along at least one axis. The detailed description of a preferred structure and its use as a backsheet on a sanitary napkin or a disposable diaper will allow one skilled in the art to readily adapt the present invention to other applications.

Figure 3:
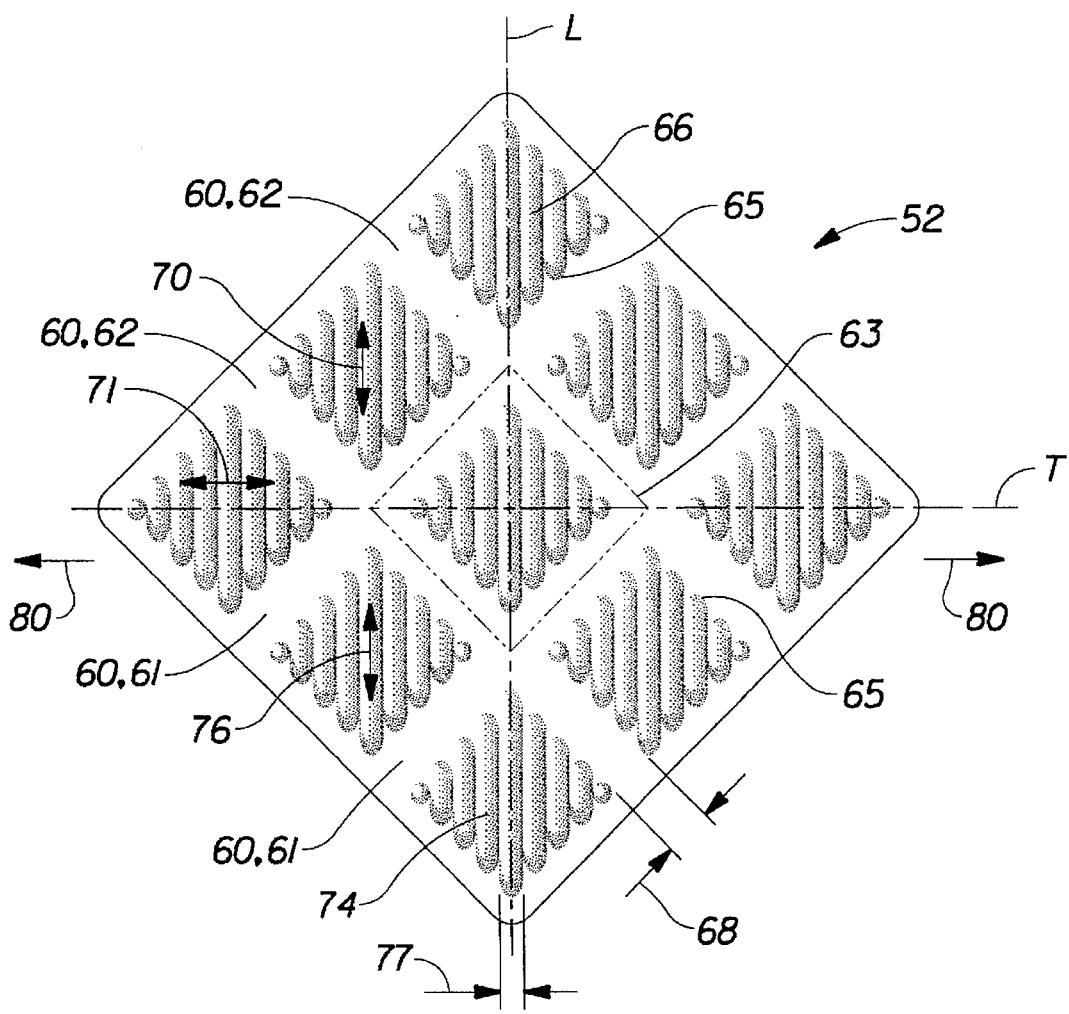
FIG. 3 is a plan view illustration of a preferred embodiment of a polymeric web material of the present invention.

Referring now to FIG. 3, there is shown a preferred embodiment of a polymeric web material 52 of the present invention. The web material 52 is shown in FIG. 3 in its substantially untensioned condition. The web material 52 is particularly well suited for use as a backsheet on an absorbent article, such as the sanitary napkin 20 in FIG. 1 or the disposable diaper 30 in FIG. 2. The web material 52 has two centerlines, a longitudinal centerline, which is also referred to hereinafter as an axis, line, or direction "L" and a transverse or lateral centerline, which is also referred to hereinafter as an axis, line, or direction "T". The transverse centerline "T" is generally perpendicular to the longitudinal centerline "L".

Web material 52 includes a "strainable network" of distinct regions. As used herein, the term "strainable network" refers to an interconnected and interrelated group of regions which are able to be extended to some useful degree in a predetermined direction providing the web material with an elastic-like behavior in response to an applied and subsequently released elongation. The strainable network includes a plurality of first regions 60 and a plurality of second regions 66. Web material 52 also includes transitional regions 65 which are located at the interface between the first regions 60 and the second regions 66. The transitional regions 65 will exhibit complex combinations of the behavior of both the first region and the second region. It is recognized that every embodiment of the present invention will have transitional regions, however, the present invention is largely defined by the behavior of the web material in distinctive regions (e.g., first regions 60 and second regions 66). Therefore, the ensuing description of the present invention will be concerned with the behavior of the web material in the first regions 60 and the second regions 66 only since it is not significantly dependent upon the complex behavior of the web material in the transitional regions 65.

Web material 52 has a first surface, (facing the viewer in FIG. 3), and an opposing second surface (not shown). In the preferred embodiment shown in FIG. 3, the strainable network includes a plurality of first regions 60 and a plurality of second regions 66. A portion of the first regions 60, indicated generally as 61, are substantially linear and extend in a first direction. The remaining first regions 60, indicated generally as 62, are substantially linear and extend in a second direction which is substantially perpendicular to the first direction. While it is preferred that the first direction be perpendicular to the second direction, other angular relationships between the first direction and the second direction may be suitable so long as the first regions 61 and 62 intersect one another. Preferably, the angles between the first and second directions ranges from about 45° to about 135°, with 90° being the most preferred. The intersection of the first regions 61 and 62 forms a boundary, indicated by phantom line 63 in FIG. 3, which completely surrounds the second regions 66.

Preferably, the width 68 of the first regions 60 is from about 0.01 inches to about 0.5 inches, and more preferably from about 0.03 inches to about 0.25 inches. However, other width dimensions for the first regions 60 may be suitable. Because the first regions 61 and 62 are perpendicular to one another and equally spaced apart, the second regions have a square shape. However, other shapes for the second region 66 are suitable and may be achieved by changing the spacing between the first regions and/or the alignment of the first regions 61 and 62 with respect to one another. The second regions 66 have a first axis 70 and a second axis 71. The first axis 70 is substantially parallel to the longitudinal axis of the web material 52, while the second axis 71 is substantially parallel to the transverse axis of the web material 52. The first regions 60 have an elastic modulus E1 and a cross-sectional area A1. The second regions 66 have an elastic modulus E2 and a cross-sectional area A2.

In the illustrated embodiment, the web material 52 has been "formed" such that the web material 52 exhibits a resistive force along an axis, which in the case of the illustrated embodiment is substantially parallel to the transverse axis of the web, when subjected to an applied axial elongation in a direction substantially parallel to the transverse axis. As used herein, the term "formed" refers to the creation of a desired structure or geometry upon a web material that will substantially retain the desired structure or geometry when it is not subjected to any eternally applied elongations or forces. A web material of the present invention is comprised of a plurality of first regions and a plurality of second regions, wherein the first regions are visually distinct from the second regions. As used herein, the term "visually distinct" refers to features of the web material which are readily discernible to the normal naked eye when the web material or objects embodying the web material are subjected to normal use. As used herein the term "surface-pathlength" refers to a measurement along the topographic surface of the region in question in a direction substantially parallel to an axis. The method for determining the surface-pathlength of the respective regions can be found in the Test Methods section set forth in subsequent portions of the present specification.

Methods for forming web materials of the present invention include, but are not limited to embossing by mating plates or rolls, thermoforming, high pressure hydraulic forming, or casting. While the entire portion of the web 52 has been subjected to a forming operation, the present invention may also be practiced by subjecting to formation only a portion thereof, e.g., a portion of a diaper backsheet, as will be described in detail below.

In the preferred embodiment shown in FIG. 3 the first regions 60 are substantially planar. That is, the material within the first regions 60 is in substantially the same condition before and after the formation step undergone by web 52. The second regions 66 include a plurality of raised rib-like elements 74. The rib-like elements 74 may be embossed, debossed or a combination thereof The rib-like elements 74 have a first or major axis 76 which is substantially parallel to the longitudinal axis of the web 52 and a second or minor axis 77 which is substantially parallel to the transverse axis of the web 52.

The rib-like elements 74 in the second region 66 may be separated from one another by unformed areas, essentially unembossed or debossed, or simply formed as spacing areas. Preferably, the rib-like elements 74 are adjacent one another and are separated by an unformed area of less than 0.10 inches as measured perpendicular to the major axis 76 of the rib-like elements 74, and more preferably, the rib-like elements 74 are contiguous having no unformed areas between them.

The first regions 60 and the second regions 66 each have a "projected pathlength". As used herein the term "projected pathlength" refers to the length of a shadow of a region that would be thrown by parallel light. The projected pathlength of the first region 60 and the projected pathlength of the second region 66 are equal to one another.

The first region 60 has a surface-pathlength, L1, less than the surface-pathlength, L2, of the second region 66 as measured topographically in a parallel direction while the web is in an untensioned condition. Preferably, the surface-pathlength of the second region 66 is at least about 15% greater than that of the first region 60, more preferably at least about 30% greater than that of the first region, and most preferably at least about 70% greater than that of the first region. In general, the greater the surface-pathlength of the second region, the greater will be the elongation of the web before encountering the force wall.

Web material 52 exhibits a modified "Poisson lateral contraction effect" substantially less than that of an otherwise identical base web of similar material composition, i.e., a web having no first and second regions. The method for determining the Poisson lateral contraction effect of a material can be found in the Test Methods section set forth in subsequent portions of the present specification. Preferably, the Poisson lateral contraction effect of webs of the present invention is less than about 0.4 when the web is subjected to about 20% elongation. Preferably, the webs exhibit a Poisson lateral contraction effect less than about 0.4 when the web is subjected to about 40, 50 or even 60% elongation. More preferably, the Poisson lateral contraction effect is less than about 0.3 when the web is subjected to 20, 40, 50 or 60% elongation. The Poisson lateral contraction effect of webs of the present invention is determined by the amount of the web material which is occupied by the first and second regions, respectively. As the area of the web material occupied by the first region increases the Poisson lateral contraction effect also increases. Conversely, as the area of the web material occupied by the second region increases the Poisson lateral contraction effect decreases. Preferably, the percent area of the web material occupied by the first region is from about 2% to about 90%, and more preferably from about 5% to about 50%.

Web materials of the prior art which have at least one layer of an elastomeric material will generally have a large Poisson lateral contraction effect, i.e., they will "neck down" as they elongate in response to an applied force. Web materials of the present invention can be designed to moderate if not substantially eliminate the Poisson lateral contraction effect.

For web material 52, the direction of applied axial elongation, D, indicated by arrows 80 in FIG. 3, is substantially perpendicular to the first axis 76 of the rib-like elements 74. This is due to the fact that the rib-like elements 74 are able to unbend or geometrically deform in a direction substantially perpendicular to their first axis 76 to allow extension in web 52.

Figure 4:
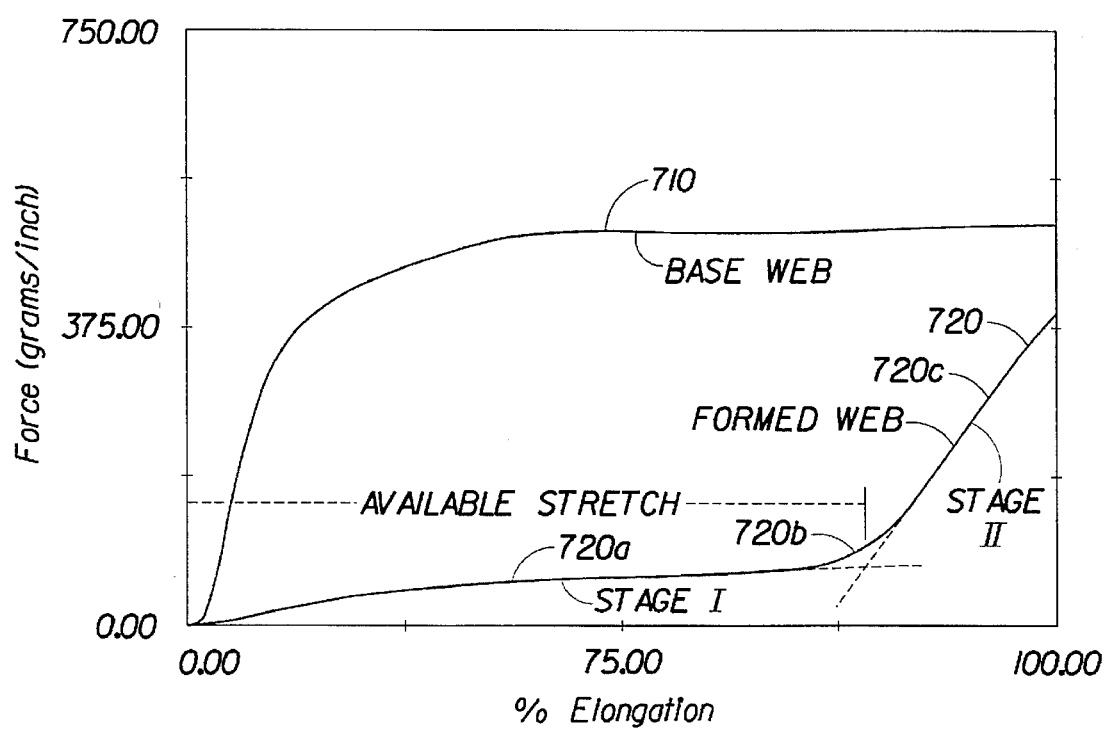
FIG. 4 is an exemplary graph of the resistive force versus percent elongation behavior of a web material of the present invention, such as shown in FIG. 3, and a base web material, i.e., which does not include first and second regions, of similar material composition.

In FIG. 4 there is shown an exemplary graph of a resistive force-elongation curve 720 of a web material generally similar to web material 52 shown in FIG. 3 along with a curve 710 of a base web material of similar composition. The method for generating resistive force-elongation curves can be found in the Test Methods section set forth in subsequent portions of the present specification. Referring now to the force-elongation curve 720 of the formed web of the present invention, there is an initial substantially linear, lower force versus elongation stage I designated 720a, a transition zone designated 720b which indicates the encounter of the force wall, and a substantially linear stage II designated 720c which displays substantially higher force versus elongation behavior.

As seen in FIG. 4 the formed web exhibits different elongation behavior in the two stages when subjected to an applied elongation in a direction parallel to the transverse axis of the web. The resistive force exerted by the formed web to the applied elongation is significantly less in the stage I region (720a) versus the stage II region (720c) of curve 720. Furthermore, the resistive force exerted by the formed web to the applied elongation as depicted in stage I (720a) of curve 720 is significantly less than the resistive force exerted by the base web as depicted in curve 710 within the limits of elongation of stage I. As the formed web is subjected to further applied elongation and enters stage II (720c) the resistive force exerted by the formed web increases and approaches the resistive force exerted by the base web. The resistive force to the applied elongation for the stage I region (720a) of the formed web is provided by the molecular-level and geometric deformation of the first region of the formed web and the geometric deformation of the second region of the formed web. This is in contrast to the resistive force to an applied elongation that is provided by the base web, depicted in curve 710 of FIG. 4, which results from molecular-level deformation of the entire web. Web materials of the present invention can be designed to yield virtually any resistive force in stage I which is less than that of the base web material by adjusting the percentage of the web surface which is comprised of the first and second regions, respectively. The force-elongation behavior of stage I can be controlled by adjusting the width, cross-sectional area, and spacing of the first region and the composition of the base web.

Figure 5:
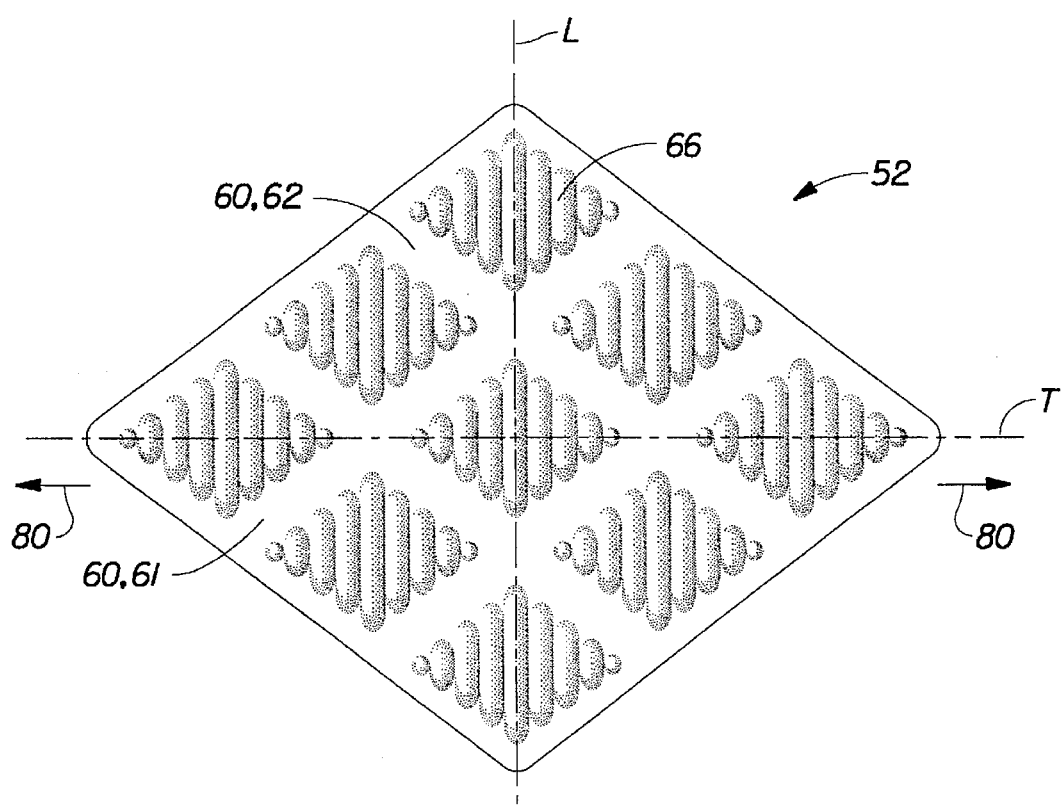
FIG. 5 is a plan view illustration of a polymeric web material of FIG. 3 in a tensioned condition corresponding to stage I on the force-elongation curve depicted in FIG. 4.

Referring now to FIG. 5, as web 52 is subjected to an applied axial elongation, D, indicated by arrows 80 in FIG. 5, the first regions 60 having the shorter surface-pathlength, L1, provide most of the initial resistive force, P1, as a result of molecular-level deformation, to the applied elongation which corresponds to stage I. While in stage I, the rib-like elements 74 in the second regions 66 are experiencing geometric deformation, or unbending and offer minimal resistance to the applied elongation. In addition, the shape of the second regions 66 changes as a result of the movement of the reticulated structure formed by the intersecting first regions 61 and 62. Accordingly, as the web 52 is subjected to the applied elongation, the first regions 61 and 62 experience geometric deformation or bending, thereby changing the shape of the second regions 66. The second regions are extended or lengthened in a direction parallel to the direction of applied elongation, and collapse or shrink in a direction perpendicular to the direction of applied elongation.

In the transition zone (720b) between stages I and II, the rib-like elements 74 are becoming aligned with, (i.e., coplanar with), the applied elongation. That is, the second region 66 is exhibiting a change from geometric deformation to molecular-level deformation. This is the onset of the force wall. In stage II, the rib-like elements 74 in the second region 66 are substantially aligned with, (i.e., coplanar with), the axis of applied elongation (i.e. the second region has reached its limit of geometric deformation) and begin to resist further elongation via molecular-level deformation. The second region 66 now contributes, as a result of molecular-level deformation, a second resistive force, P2, to further applied elongation. In stage II, the first regions 61 and 62 have also reached their limit of geometric deformation and resist further elongation mainly via molecular-level deformation. The resistive forces to elongation depicted in stage II by both the molecular-level deformation of the first regions 60 and the molecular-level deformation of the second regions 66 provide a total resistive force, PT, which is greater than the resistive force depicted in stage I which is provided by the molecular-level and geometric deformation of the first regions 60 and the geometric deformation of the second regions 66. Accordingly, the slope of the force-elongation curve in stage II is significantly greater than the slope of the force-elongation curve in stage I.

The resistive force P1 is substantially greater than the resistive force P2 when (L1+D) is less than L2. When (L1+D) is less than L2 the first region provides the initial resistive force P1, generally satisfying the equation:

$$P1 = \frac{(A1 \times E1 \times D)}{L1}$$

When (L1+D) is greater than L2 the first and second regions provide a combined total resistive force PT to the applied elongation, D, generally satisfying the equation:

$$PT = \frac{(A1 \times E1 \times D)}{L1} + \frac{(A2 \times E2 \times |L1 + D - L2|)}{L2}$$

The maximum elongation occurring while in stage I is referred to as the "available stretch" of the formed web material. The available stretch corresponds to the distance over which the second region experiences geometric deformation. The available stretch can be effectively determined by inspection of the force-elongation curve 720 as shown in FIG. 4. The approximate point at which there is an inflection in the transition zone between stage I and stage II is the percent elongation point of "available stretch". The range of available stretch can be varied from about 10% to 100% or more; this range of elongation is often found to be of interest in disposable absorbent articles, and can be largely controlled by the extent to which the surface-pathlength L2 in the second region exceeds the surface-pathlength L1 in the first region and the composition of the base film. The term available stretch is not intended to imply a limit to the elongation which the web of the present invention may be subjected to as there are applications where elongation beyond the available stretch is desirable.

Figure 6:
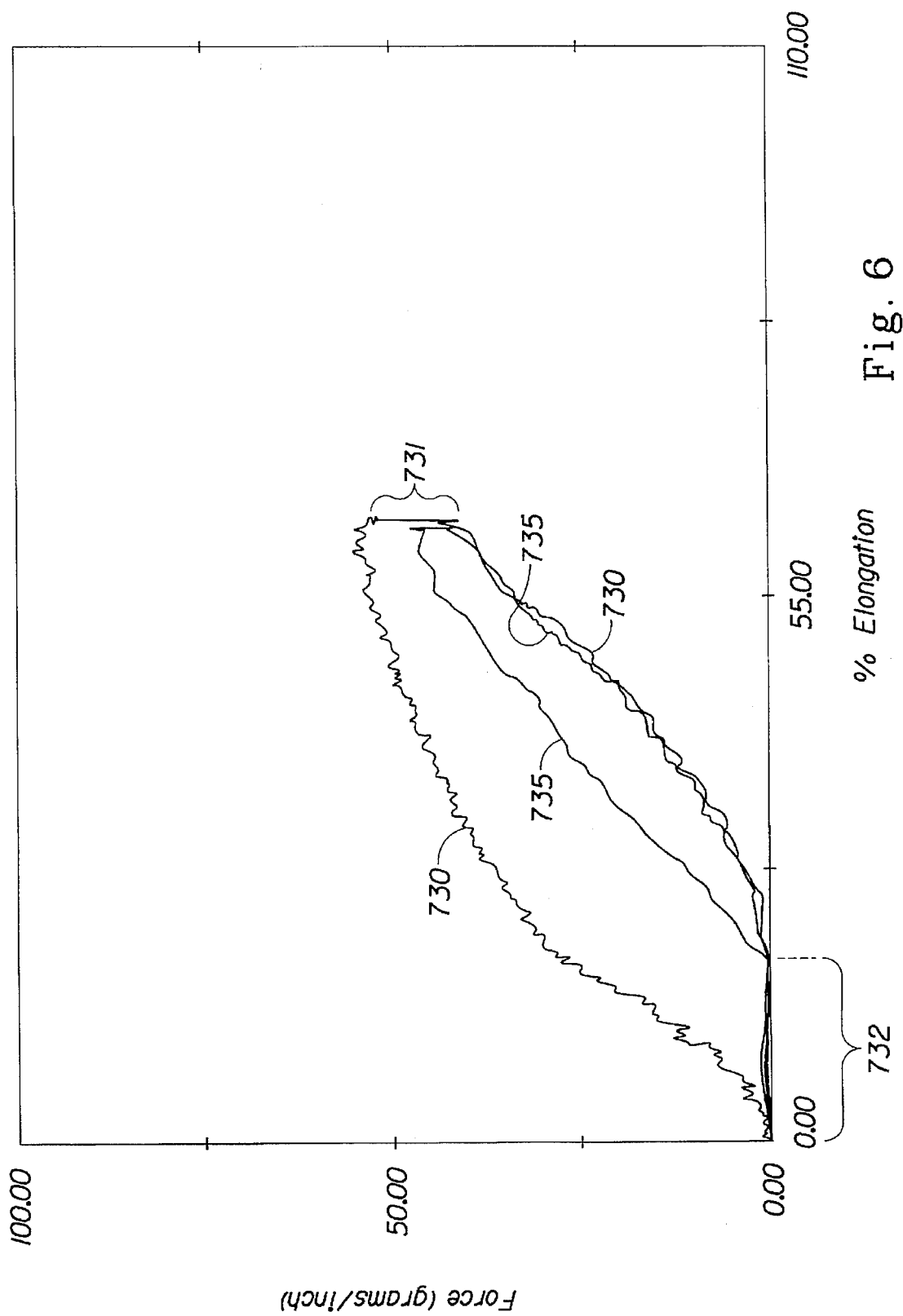
FIG. 6 is an exemplary graph of the elastic hysteresis behavior of the web material of the present invention which is graphically represented by curve 720 in FIG. 4 when the web material is subjected to a hysteresis test at 60% elongation.

The curves 730 and 735 in FIG. 6 show an exemplary elastic hysteresis behavior exhibited by a web material of the present invention. Curve 730 represents the response to an applied and released elongation during the first cycle and curve 735 represent the response to an applied and released elongation during the second cycle. The force relaxation during the first cycle 731 and the percent set or deformation 732 are depicted in FIG. 6. Note that significant recoverable elongation, or useful elasticity, is exhibited at relatively low forces over multiple cycles, i.e., the web material can easily expand and contract to a considerable degree. The method for generating the elastic hysteresis behavior can be found in the Test Method section set forth in subsequent portion of the present specification.

When the web material is subjected to an applied elongation, the web material exhibits an elastic-like behavior as it extends in the direction of applied elongation and returns to its substantially untensioned condition once the applied elongation is removed, unless the web material is extended beyond the point of yielding. The web material is able to undergo multiple cycles of applied elongation without losing its ability to substantially recover. Accordingly, the web is able to return to its substantially untensioned condition once the applied elongation is removed.

While the web material may be easily and reversibly extended in the direction of applied axial elongation, in a direction substantially perpendicular to the first axis 76 of the rib-like elements 74, the web material is not as easily extended in a direction substantially parallel to the first axis 76 of the rib-like elements 74. The formation of the rib-like elements allows the rib-like elements to geometrically deform in a direction substantially perpendicular to the first or major axis 76 of the rib-like elements, while requiring substantially molecular-level deformation to extend in a direction substantially parallel to the first axis of the rib-like elements.

The amount of applied force required to extend the web is dependent upon the composition and cross-sectional area of the web material and the width and spacing of the first regions, with narrower and more widely spaced first regions requiring lower applied extensional forces to achieve the desired elongation for a given composition and cross-sectional area.

The depth and frequency of rib-like elements can also be varied to control the available stretch of a web of the present invention. The available stretch is increased if for a given frequency of rib-like elements, the height or degree of formation imparted on the rib-like elements is increased. Similarly, the available stretch is increased if for a given height or degree of formation, the frequency of the rib-like elements is increased.

There are several functional properties that can be controlled through the application of the present invention. The functional properties are the resistive force exerted by the web material against an applied elongation and the available stretch of the web material before a force wall is encountered. The resistive force that is exerted by the web material against an applied elongation is a function of the material (e.g., composition, molecular structure and orientation, etc.) and cross-sectional area and the percent of the projected surface area of the web material that is occupied by the first region. The higher the percent area coverage of the web material by the first region, the higher the resistive force that the web will exert against an applied elongation for a given material composition and cross-sectional area. The percent coverage of the web material by the first region is determined in part if not wholly by the widths of the first regions and the spacing between adjacent first regions.

The available stretch of the web material is determined by the surface-pathlength of the second region. The surface-pathlength of the second region is determined at least in part by the rib-like element spacing, rib-like element frequency and depth of formation of the rib-like elements as measured perpendicular to the plane of the web material. In general, the greater the surface-pathlength of the second region the greater the available stretch of the web material.

In addition to the aforementioned elastic-like properties, a plastic film of the present invention is also characterized as being soft, cloth-like in texture and appearance, and quiet. The soft, cloth-like, quiet, plastic film is also a liquid barrier making it especially useful as a backsheet on a disposable absorbent article, such as a disposable diaper.

While an entire web material of the present invention may include a strainable network of first and second regions, the present invention may also be practiced by providing only specific portions of the web with a strainable network comprised of first and second regions. It will be obvious to one skilled in the art that all or a portion of a backsheet on a disposable absorbent article may include a strainable network(s) comprised of first and second regions.

While the web material having a strainable network of the present invention has been described as a backsheet or a portion thereof on an absorbent article, in some embodiments it may be necessary to provide the topsheet and the absorbent core with a strainable network.

Method of Making

Figure 7:
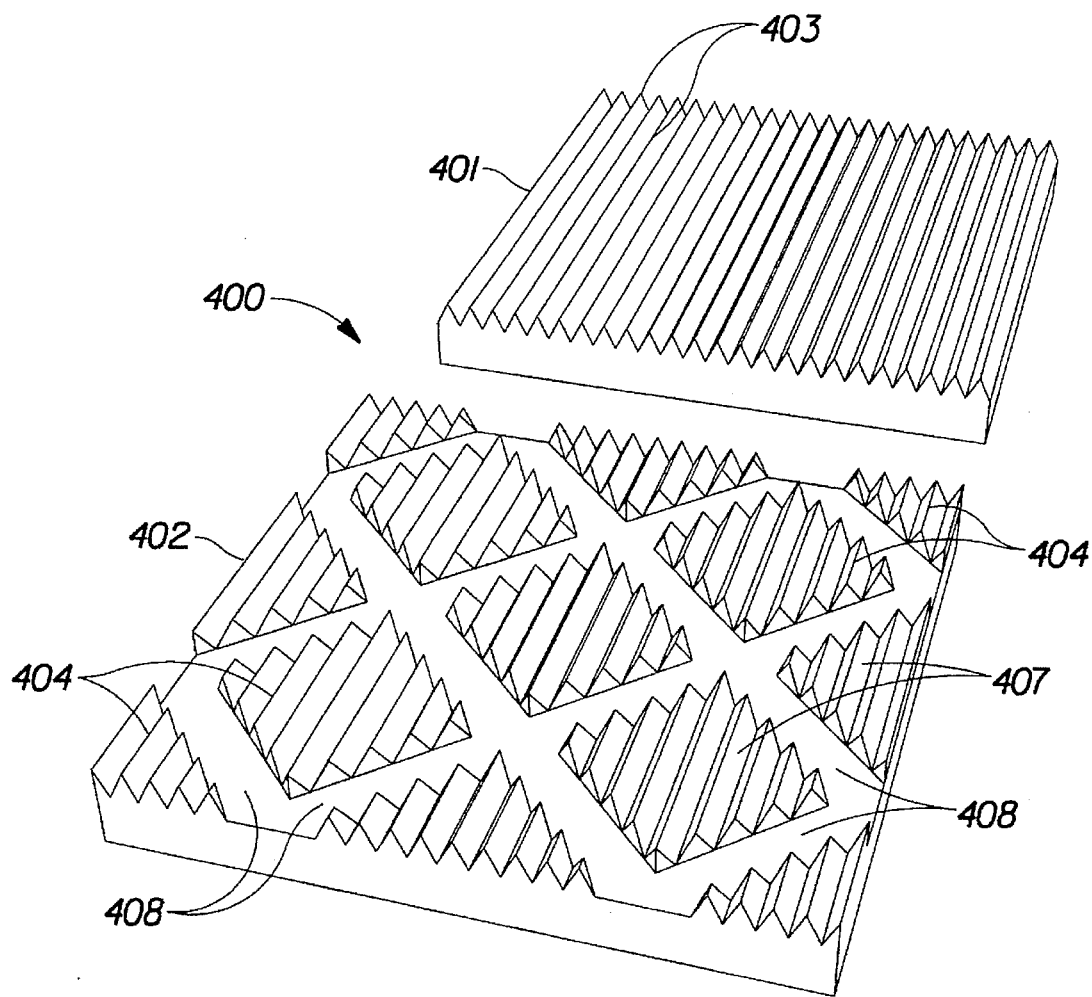
FIG. 7 is a simplified perspective view of a preferred apparatus used to form web materials of the present invention with a portion of the apparatus being tilted to expose the teeth.

Referring now to FIG. 7, there is shown an apparatus 400 used to form the web 52 shown in FIG. 3. Apparatus 400, includes intermeshing plates 401, 402. Plates 401, 402 include a plurality of intermeshing teeth 403, 404, respectively. Plates 401, 402 are brought together under pressure to form the web of the present invention.

Plate 402 includes toothed regions 407 and grooved regions 408. Within toothed regions 407 of plate 402 there are a plurality of teeth 404. Plate 401 includes teeth 403 which mesh with teeth 404 of plate 402. When a film is formed between plates 401, 402 the portions of the film which are positioned within grooved regions 408 of plate 402 and teeth 403 on plate 401 remain undeformed. These regions correspond with the first regions 60 of web 52 shown in FIG. 3. The portions of the film positioned between toothed regions 407 of plate 402, (which comprise teeth 404), and teeth 403 of plate 401 are incrementally and plastically formed creating rib-like elements 74 in the second regions 66 of web material 52.

The method of formation can be accomplished in a static mode, where one discrete portion of a base film is deformed at a time. Alternatively, the method of formation can be accomplished using a continuous, dynamic press for intermittently contacting the moving web and forming the base material into a formed web material of the present invention. These and other suitable methods for forming the web material of the present invention are more fully described in U.S. Pat. No. 5,518,801 issued to Chappell, et al. on May 21, 1996 and is hereby incorporated herein by reference.

Web materials of the present invention may be comprised of polyolefins such as polyethylenes, including linear low density polyethylene (LLDPE), low density polyethylene (LDPE), ultra low density polyethylene (LLDPE), high density polyethylene (HDPE), or polypropylene and blends thereof with the above and other materials. Examples of other suitable polymeric materials which may also be used include, but are not limited to, polyester, polyurethanes, compostable or biodegradable polymers, heat shrink polymers, thermoplastic elastomers, metallocene catalyst-based polymers (e.g., INSITE® available from Dow Chemical Company and Exxact® available from Exxon), and breathable polymers. The web material may also be comprised of a synthetic woven, synthetic knit, nonwoven, apertured film, macroscopically expanded three-dimensional formed film, absorbent or fibrous absorbent material, foam, filled composition, or laminates and/or combinations thereof. The nonwovens may be made by but not limited to any of the following methods: spunlace, spunbond, meltblown, carded and/or air-through or calendar bonded, with a spunlace material with loosely bound fibers being the preferred embodiment.

While the present invention has been described as providing a web material from a single layer of base film, the present invention may be practiced equally well with other materials. While the fluid impervious polymeric film exhibiting an elastic-like behavior in the direction of applied elongation may be suitable for use a backsheet on a disposable diaper or sanitary napkin, such a web material would not function well as a topsheet on an absorbent article. Examples of other base materials from which the web of the present invention can be made and will function effectively as a fluid pervious topsheet on an absorbent article include two-dimensional apertured films and macroscopically expanded, three-dimensional, apertured formed films. Examples of macroscopically expanded, three-dimensional, apertured formed films are described in U.S. Pat. No. 3,929,135, issued to Thompson on Dec. 30, 1975; U.S. Pat. No. 4,324,246 issued to Mullane, et al. on Apr. 13, 1982; U.S. Pat. No. 4,342,314 issued to Radel, et al. on Aug. 3, 1982; U.S. Pat. No. 4,463,045 issued to Ahr, et al. on Jul. 31, 1984; and U.S. Pat. No. 5,006,394 issued to Baird on Apr. 9, 1991. Each of these patents are incorporated herein by reference.

Web materials of the present invention may include laminates of the above mentioned materials. Laminates may be combined by any number of bonding methods known to those skilled in the art. Such bonding methods include but are not limited to thermal bonding, adhesive bonding (using any of a number of adhesives including but not limited to spray adhesives, hot melt adhesives, latex based adhesives and the like), sonic bonding and extrusion laminating whereby a polymeric film is cast directly onto a substrate, and while still in a partially molten state, bonds to one side of the substrate, or by depositing meltblown fibers nonwoven directly onto a substrate.

Test Methods
Surface-Pathlength

Pathlength measurements of formed material regions are to be determined by selecting and preparing representative samples of each distinct region and analyzing these samples by means of microscopic image analysis methods.

Samples are to be selected so as to be representative of each region's surface geometry. Generally, the transition regions should be avoided since they would normally contain features of both the first and second regions. The sample to be measured is cut and separated from the region of interest. The "measured edge" is to be cut parallel to a specified axis of elongation. An unstriated sample length of one-half inch is to be "gauge marked" perpendicular to the "measured edge": while attached to the web material, and then accurately cut and removed from the web material.

Measurement samples are then mounted onto the long-edge of a microscopic glass slide. The "measured edge" is to extend slightly (approximately 1 mm) outward from the slide edge. A thin layer of pressure-sensitive adhesive is applied to the glass face-edge to provide a suitable sample support means. For highly formed sample regions it has been found desirable to gently extend the sample in its axial direction (without imposing significant force) simultaneous to facilitate contact and attachment of the sample to the slide-edge. This allows improved edge identification during image analysis and avoids possible "crumpled" edge portions that require additional interpretation analysis.

Images of each sample are to be obtained as "measured edge" views taken with the support slide "edge on" using suitable microscopic measuring means of sufficient quality and magnification. Data is obtained using the following equipment; Keyence VH-6100 (20× Lens) video unit, with video-image prints made with a Sony Video printer Mavigraph unit. Video prints were image-scanned with a Hewlett Packard ScanJet IIP scanner. Image analysis was on a Macintosh IICi computer utilizing the software NIH MAC Image version 1.45.

Using this equipment, a calibration image initially taken of a grid scale length of 0.500" with 0.005" increment-marks to be used for calibration setting of the computer image analysis program. All samples to be measured are then video-imaged and video-image printed. Next, all video-prints are image-scanned at 100 dpi (256-level gray scale) into a suitable Mac image-file format. Finally, each image-file (including calibration file) is analyzed utilizing MaC Image 1.45 computer program. All samples are measured with freehand line-measurement tool selected. Samples are measured on both side-edges and the lengths are recorded. Simple film-like (thin & constant thickness) samples require only one side-edge to be measured. Laminate and thick foam samples are measured on both side-edges. Length measurement tracings are to be made along the full gauge length of a cut sample. In cases of highly deformed samples, multiple (partially overlapping) images may be required to cover the entire cut sample. In these cases, select characteristic features common to both overlapping-images and utilize as "markers" to permit image length readings to adjoin but not overlap.

The final determination of surface-pathlength for each region is obtained by averaging the lengths of five (5) separate ½ gauge-samples of each region. Each gauge-sample "surface-pathlength" is to be the average of both side-edge surface-pathlengths.

Poisson's Lateral Contraction Effect

The Poisson's lateral contraction effect is measured on an Instron Model 1122, as available from Instron Corporation of Canton, Mass., which is interfaced to a Gateway 2000 486/33 Hz computer available from Gateway 2000 of N. Sioux City, S.D., using Test Works™ software which is available from Sintech, Inc. of Research Triangle Park, N.C. All essential parameters needed for testing are input in the Test works™ software for each test. Data collection is accomplished through a combination of manual sample width measurements, and elongation measurements made within TestWorks™.

The samples used for this test are 1" wide×4" long with the long axis of the sample cut parallel to the direction of the first region of the sample. The sample should be cut with a sharp knife or suitably sharp cutting device designed to cut a precise 1" wide sample. It is important that a "representative sample" should be cut so that an area representative of the symmetry of the overall pattern of the deformed region is represented. There will be cases (due to variations in either the size of the deformed portion or the relative geometries of regions 1 and 2) in which it will be necessary to cut either larger or smaller samples than is suggested herein. In this case, it is very important to note (along with any data reported) the size of the sample, which area of the deformed region it was taken from and preferably include a schematic of the representative area used for the sample. In general, an "aspect ratio" of (2:1) for the actual extended tensile portion (l1:w1) is to be maintained if possible. Five samples are tested.

The grips of the Instron consist of air actuated grips designed to concentrate the entire gripping force along a single line perpendicular to the direction of testing elongation having one flat surface and an opposing face from which protrudes a half round. No slippage should be permitted between the sample and the grips. The distance between the lines of gripping force should be 2" as measured by a steel rule held beside the grips. This distance will be referred to from here on as the "gauge length".

The sample is mounted in the grips with its long axis perpendicular to the direction of applied elongation. An area representative of the overall pattern geometry should be symmetrically centered between the grips. The crosshead speed is set to 10 in/min. The crosshead moves to the specified strain (measurements are made at both 20 and 60% elongation). The width of the sample at its narrowest point (w2) is measured to the nearest 0.02" using a steel rule. The elongation in the direction of applied extension is recorded to the nearest 0.02" on the TestWorks software. The Poisson's Lateral Contraction Effect (PLCE) is calculated using the following formula:

$$PLCE = \frac{\frac{|w2 - w1|}{w1}}{\frac{|l2 - l1|}{l1}}$$

where w2=The width of the sample under an applied longitudinal elongation;

w1=The original width of the sample;

l2=The length of the sample under an applied longitudinal elongation; and l1=The original length of the sample (gauge length);

Measurements are made at both 20 and 60% elongation using five different samples for each given elongation. The PLCE at a given percent elongation is the average of five measurements.

Hysteresis Test

The hysteresis test is used for measuring the percent set and percent force relaxation of a material. The tests are performed on an Instron Model 1122, available from Instron Corporation of Canton, Mass. which is interfaced to a Gateway 2000 486/33 Hz computer available from Gateway 2000 of N. Sioux City, S.D. 57049, using TestWorks™ software which is available from Sintech, Inc. of Research Triangle Park, N.C. 27709. All essential parameters needed for testing are input in the TestWorks™ software for each test (i.e. Crosshead Speed, Maximum percent elongation Point and Hold Times). Also, all data collection, data analysis and graphing are done using the TestWorks™ software.

The samples used for this test are 1" wide×4" long with the long axis of the sample cut parallel to the direction of maximum extensibility of the sample. The sample should be cut with a sharp exacto knife or some suitably sharp cutting device design to cut a precise 1" wide sample. (If there is more than one direction of elongation of the material, samples should be taken parallel to representative directions of elongation). The sample should be cut so that an area representative of the symmetry of the overall pattern of the deformed region is represented. There will be cases (due to variations in either the size of the deformed portion or the relative geometries of the first and second regions) in which it will be necessary to cut either larger or smaller samples than is suggested herein. In this case, it is very important to note (along with any data reported) the size of the sample, which area of the deformed region it was taken from and preferably include a schematic of the representative area used for the sample. Three separate tests at 20, 60 and 100% strain are typically measured for each material. Three samples of a given material are tested at each percent elongation.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2" as measured by a steel rule held beside the grips. This distance will be referred to from hereon as the "gauge length". The sample is mounted in the grips with its long axis perpendicular to the direction of applied percent elongation. The crosshead speed is set to 10 in/min. The crosshead moves to the specified maximum percent elongation and holds the sample at this percent elongation for 30 seconds. After the thirty seconds the crosshead returns to its original position (0% elongation) and remains in this position for 60 seconds. The crosshead then returns to the same maximum percent elongation as was used in the first cycle, holds for thirty seconds and then again returns to zero.

A graph of two cycles is generated. The percent force relaxation is determined by the following calculation of the force data from the first cycle:

$$\frac{\text{Force at Max. \% elongation} - \text{Force after 30 sec. hold} \times 100}{\text{Force at Maximum \% elongation (cycle 1)}} = \% \text{ Force Relaxation}$$

The percent set is the percent elongation of the sample of the second cycle where the sample starts to resist the elongation. The average percent force relaxation and percent set for three samples is reported for each maximum percent elongation value tested.

Tensile Test

The tensile test is used for measuring force versus percent elongation properties and percent available stretch of a material. The tests are performed on an Instron Model 1122, available from Instron Corporation of Canton, Mass. which is interfaced to a Gateway 2000 486/33 Hz computer available from Gateway 2000 of N. Sioux City, S.D., using TestWorks™ software which is available from Sintech, Inc. of Research Triangle Park, N.C. All essential parameters needed for testing are input in the TestWorks™ software for each test. Also, all data collection, data analysis and graphing are done using the TestWorks™ software.

The samples used for this test are 1" wide×4" long with the long axis of the sample cut parallel to the direction of maximum extensibility of the sample. The sample should be cut with a sharp exacto knife or some suitably sharp cutting device design to cut a precise 1" wide sample. (If there is more than one direction of extensibility of the material, samples should be taken parallel to representative direction of elongation). The sample should be cut so that an area representative of the symmetry of the overall pattern of the deformed region is represented. There will be cases (due to variations in either the size of the deformed portion or the relative geometries of regions 1 and 2) in which it will be necessary to cut either larger or smaller samples than is suggested herein. In this case, it is very important to note (along with any data reported) the size of the sample, which area of the deformed region it was taken from and preferably include a schematic of the representative area used for the sample. Three samples of a given material are tested.

The grips of the Instron consist of air actuated grips designed to concentrate the entire gripping force along a single line perpendicular to the direction of testing stress having one flat surface and an opposing face from which protrudes a half round to minimize slippage of the sample. The distance between the lines of gripping force should be 2" as measured by a steel rule held beside the grips. This distance will be referred to from hereon as the "gauge length". The sample is mounted in the grips with its long axis perpendicular to the direction of applied percent elongation. The crosshead speed is set to 10 in/min. The crosshead elongates the sample until the sample breaks at which point the crosshead stops and returns to its original position (0% elongation).

The percent available stretch is the point at which there is an inflection in the force—elongation curve, beyond which point there is a rapid increase in the amount of force required to elongate the sample further. The average of the percent available stretch for three samples is recorded.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A soft web material comprising: a plurality of first regions and a plurality of second regions being comprised of the same material composition, a portion of said first regions extending in a first direction while the remainder of said first regions extend in a second direction perpendicular to said first direction to intersect one another, said first regions forming a boundary completely surrounding said second regions, said second regions comprising a plurality of raised rib-like elements, said first regions undergoing a molecular-level and geometric deformation and said second regions initially undergoing a substantially geometric deformation when said web material is subjected to an applied elongation along at least one axis.

2. The web material of claim 1, wherein said first regions and said second regions are distinct from one another.

3. The web material of claim 1, wherein said first region is substantially free of said rib-like elements.

4. The web material of claim 1, wherein said rib-like elements have a major axis and a minor axis.

5. The web material of claim 3, wherein said first region and said second region are comprised of at least one layer of film material.

6. The web material of claim 5, wherein said film material is comprised of polyethylene or blends thereof.

7. A soft web material exhibiting an elastic-like behavior along at least one axis, said web material comprising: a plurality of first regions and a plurality of second regions, said first region and said second region being comprised of the same material composition and each having an untensioned projected pathlength, a portion of said first regions extending in a first direction while the remainder of said first regions extend in a second direction perpendicular to said first direction to intersect one another, said first regions forming a boundary completely surrounding said second regions, said second regions comprising a plurality of raised rib-like elements, said first region undergoing a molecular-level and geometric deformation and said second region initially undergoing a substantially geometric deformation when said web material is subjected to an applied elongation in a direction substantial parallel to said axis, said first region and said second region substantially returning to their untensioned projected pathlength when said applied elongation is released.

8. The web material of claim 7, wherein said first regions and said second regions are distinct from one another.

9. The web material of claim 7, wherein said first region is substantially free of said rib-like elements.

10. The web material of claim 7, wherein said rib-like elements have a major axis and a minor axis.

11. The web material of claim 7, wherein said first region and said second region are comprised of at least one layer of film material.

12. The web material of claim 11, wherein said film material is comprised of polyethylene or blends thereof.

13. The web material of claim 7, wherein said web material has an available stretch.

14. The web material of claim 13, wherein said second region provides a limit to said available stretch.

15. The web material of claim 7, wherein said web material is a backsheet on a disposable absorbent article.

16. The web material of claim 7, wherein said web material is a portion of a backsheet on a disposable absorbent article.

17. The web material of claim 7, wherein said web material is a topsheet on a disposable absorbent article.

18. The web material of claim 7, wherein said web material is a portion of a topsheet on a disposable absorbent article.

19. The web material of claim 7, wherein said web material is a laminate of two or more materials.

20. A soft web material exhibiting at least two-stages of resistive forces to an applied axial elongation along at least one axis when subjected to the applied axial elongation in a direction substantially parallel to said axis, said web material comprising: a strainable network of visually distinct regions, said strainable network including a plurality of regions and a plurality of second regions, said first region and said second region being comprised of the same material composition and each having a surface-pathlength, a portion of said first regions extending in a first direction while the remainder of said first regions extend in a second direction perpendicular to said first direction to intersect one another, said first regions forming a boundary completely surrounding said second regions, said second regions comprising a plurality of raised rib-like elements, said surface-pathlength of said first region being less than that of said second region as measured parallel to said axis while said web material is in an untensioned condition, said web material exhibiting a Poisson lateral contraction effect less than about 0.4 at 20 percent elongation as measured perpendicular to said axis.

21. The web material of claim 20, wherein said web material exhibits a Poisson lateral contraction effect less than about 0.4 at 60 percent elongation as measured perpendicular to said axis.

22. The web material of claim 20, wherein said surface-pathlength of said second region is at least about 15 percent greater than that of said first region as measured parallel to said axis while said web material is in an untensioned condition.

23. The web material of claim 20, wherein said web material is a backsheet on a disposable absorbent article.

24. The web material of claim 20, wherein said web material is a fluid pervious topsheet on a disposable absorbent article.

25. A soft web material exhibiting at least two-stages of resistive forces to an applied axial elongation, D, along at least one axis when subjected to the applied axial elongation along said axis, said web material comprising: a strainable network of visually distinct regions, said strainable network including a plurality of first regions and a plurality of second regions, a portion of said first regions extending in a first direction while the remainder of said first regions extend in a second direction perpendicular to said first direction to intersect one another, said first regions forming a boundary completely surrounding said second regions, said second regions comprising a plurality of raised rib-like elements, said first regions having a first surface-pathlength, $L1$, as measured parallel to said axis while said web material is in an untensioned condition, said second region having a second surface-pathlength, $L2$, as measured parallel to said axis while said web material is in an untensioned condition, said first surface-pathlength, $L1$, being less than said second surface-pathlength, $L2$, said first region producing by itself a resistive force, $P1$, in response to an applied axial elongation, $D$, said second region producing by itself a resistive force, $P2$, in response to said applied axial elongation, $D$, said resistive force $P1$ being substantially greater than said resistive force $P2$ when $(L1+D)$ is less than $L2$.

26. The web material of claim 25, wherein said first region has a cross-sectional area $A1$ and said second region has a cross-sectional area $A2$.

27. The web material of claim 25, wherein said first region has an elastic modulus $E1$ and said second region has an elastic modulus $E2$ when $(L1+D)$ is greater than $L2$.

28. The web material of claim 25, wherein said first region provides an initial resistive force $P1$ to the applied axial elongation D generally satisfying the equation $P1=(A1 \times E1 \times D)/L1$ when $(L1+D)$ is less than $L2$ and when $(L1+D)$ is greater than $L2$ said first and second regions providing a combined resistive force $PT$ to the applied axial elongation $D$ generally satisfying the equation $PT=((A1 \times E1 \times D)/L1)+((A2 \times E2 \times |L1+D-L2|)/L2)$.

29. A soft web material exhibiting an elastic-like behavior in response to an applied axial elongation along at least one axis thereof, said web material comprising: a strainable network having first and second regions formed of the same material composition, a portion of said first regions extending in a first direction while the remainder of said first regions extend in a second direction perpendicular to said first direction to intersect one another, said first regions forming a boundary completely surrounding said second regions, said second regions comprising relieved elements, said first regions providing a first, elastic-like resistive force to said applied elongation, and said second regions providing a second distinctive resistive force to further applied axial elongation, thereby providing at least two stages of resistive forces in use.

30. The web material of claim 29, wherein said web material comprises a transition region.

* * * * *

UNITED STATES PATENT AND TRADEMARK OFFICE
CERTIFICATE OF CORRECTION

PATENT NO. : 5,650,214  Page 1 of 2
DATED : July 22, 1997
INVENTOR(S) : Barry J. Anderson, et al It is certified that error appears in the above-identified patent and that said Letters Patent is hereby corrected as shown below:

*Column 3, line 66, "surfaces-pathlength" should read --surface-pathlength--.*
*Column 4, line 62, "deafly" should read --clearly--.*
*Column 5, line 37, "deafly" should read --clearly--.*
*Column 5, line 65, "deafly" should read --clearly--.*
*Column 7, line 56, "eternally" should read --externally--.*
*Column 11, line 41, "requiting" should read --requiring--.*
*Column 11, line 49, "requiting" should read --requiring--.*
*Column 13, line 2, "LLDPE" should read --ULDPE--.*
*Column 13, line 14, "ribrous" should read --fibrous--.*
*Column 13, line 19, "ribers" should read --fibers--.*
*Column 13, line 53, "ribers" should read --fibers--.*
*Column 13, line 67, "unstriated" should read --unstrained--.*
*Column 14, line 33, "MaC" should read --Mac--.*

UNITED STATES PATENT AND TRADEMARK OFFICE
CERTIFICATE OF CORRECTION

PATENT NO.   : 5,650,214
DATED        : July 22, 1997
INVENTOR(S)  : Barry J. Anderson, et al It is certified that error appears in the above-identified patent and that said Letters Patent is hereby corrected as shown below:

*Column 14, line 41, "eases" should read --cases--.*

*Column 14, line 49, "1/2" should read --1/2"--.*

*Column 18, line 12, "substantial" should read --substantially--.*

Signed and Sealed this

Seventeenth Day of August, 1999

Attest:

Q. TODD DICKINSON

*Attesting Officer*   *Acting Commissioner of Patents and Trademarks*